US006337310B1

(12) United States Patent
Campbell et al.

(10) Patent No.: US 6,337,310 B1
(45) Date of Patent: Jan. 8, 2002

(54) ALKYLBENZENE FROM PREISOMERIZED NAO USABLE IN LOB AND HOB SULFONATE

(75) Inventors: Curtis B. Campbell, Hercules, CA (US); Jean-Louis Marie Le Coent, Le Havre (FR)

(73) Assignees: Chevron Oronite Company LLC, San Francisco, CA (US); Chevron Oronite S.A. (FR)

( * ) Notice: Subject to any disclaimer, the term of this patent is extended or adjusted under 35 U.S.C. 154(b) by 0 days.

(21) Appl. No.: 09/585,906

(22) Filed: Jun. 2, 2000

(51) Int. Cl.⁷ ................. C10M 159/24; C07C 15/107
(52) U.S. Cl. ............................ 508/391; 585/24
(58) Field of Search ............... 585/24; 508/391

(56) References Cited

U.S. PATENT DOCUMENTS

| 4,764,295 A | * | 8/1988 | LeCoent | 252/33.2 |
|---|---|---|---|---|
| 5,071,576 A | * | 12/1991 | Vernet et al. | 252/33.4 |
| 5,112,506 A | * | 5/1992 | Marsh et al. | 252/33.4 |
| 5,137,648 A | * | 8/1992 | Marsh et al. | 252/33.4 |
| 5,578,235 A | * | 11/1996 | Jao et al. | 508/391 |
| 5,792,732 A | * | 8/1998 | Jao et al. | 508/391 |
| 5,939,594 A | | 8/1999 | LeCoent | 585/24 |
| 6,054,419 A | | 4/2000 | LeCoent | 508/391 |

FOREIGN PATENT DOCUMENTS

| EP | 0 976 810 | 2/2000 | ........ C10M/135/10 |
|---|---|---|---|
| FR | 2 564 830 | 11/1985 | .......... C07C/143/10 |
| FR | 2 752 838 | 3/1998 | ... C07C/309/24 .. |

* cited by examiner

Primary Examiner—Ellen M. McAvoy
(74) Attorney, Agent, or Firm—Linda A. Stokley; Walter L. Stumpf; Richard J. Sheridan

(57) ABSTRACT

An alkylaryl composition wherein the aryl radical is other than phenol and wherein the alkyl radical is derived from an isomerized $C_{14}$ to $C_{40}$ normal alpha olefin and wherein either (1) the weight percent of the aryl radical fixed at position 1 or 2 of a linear alkyl chain is less than about 23, or (2) at least 28 weight percent of the alkyl radicals are branched chain alkyl radicals, or (3) both is useful for making alkaline earth alkylaryl sulfonates that can be used as lubricating oil additives.

35 Claims, No Drawings

ALKYLBENZENE FROM PREISOMERIZED NAO USABLE IN LOB AND HOB SULFONATE

BACKGROUND OF THE INVENTION

In the prior art, methods are known for preparing weakly or strongly superalkalinized sulfonates from sulfonic acids obtained by the sulfonation of different alkylaryl hydrocarbons and from an excess of alkaline earth base. The alkylaryl hydrocarbons subjected to the sulfonation reaction are obtained by alkylation via the Friedel-Crafts reaction of different aryl hydrocarbons, particularly aromatic hydrocarbons, with two different types of olefin. The first type of olefins are branched olefins obtained by the oligo-polymerization of propylene to $C_{15}$ to $C_{24}$ hydrocarbons, particularly the propylene tetrapolymer dimerized to a $C_{24}$ olefin. The second type are linear olefins obtained by the oligo-polymerization of ethylene to $C_{14}$ to $C_{40}$ hydrocarbons.

It is easy to obtain a good dispersion in the medium of the alkaline earth base not fixed in the form of salt if the alkylaryl sulfonic acid is derived from a hydrocarbon obtained by alkylation of an aryl hydrocarbon with a branched olefin. However, dispersion is particularly difficult when a high percentage of the alkylaryl hydrocarbon has the aryl substituent on positions 1 or 2 of a linear alkyl chain, due to the formation of a skin when exposed to open air. This poor dispersion is especially pronounced if the medium also contains a high proportion of sulfonate, that is, if it corresponds to a low Base Number (between 3 and 60), hence to a low content of free lime and the absence of carbon dioxide and carbonate.

In fact, during the alkylation reaction with benzene or another aromatic or aryl hydrocarbon and a linear olefin, 25 mole % of the alkylaryl hydrocarbon has the aryl substituent on positions 1 or 2 of the linear alkyl chain. Traditionally, aromatics attached at the 2-position of the alkyl group give the most absorption of water. When prepared by the method described, for example in French Patent No. 2,564,830, this high proportion of alkylaryl hydrocarbon having an aryl radical on position 1 or 2 of the linear alkyl chain results in a sulfonate that exhibits hygroscopic properties such that a superficial 'skin' is formed. This 'skin' makes this product unacceptable as an additive for lubricating oil. Furthermore, the formation of this superficial skin is generally accompanied by a very low filtration rate, a high viscosity, a low incorporation of calcium, a deterioration of anti-rust performance, and an undesirable turbid appearance, or even sedimentation, when the sulfonate thus prepared is added at the rate of 10% by weight to a standard lubricating oil and stored for examination.

Chromatographic analysis has been conducted to identify each of the different isomers differing by the position of the aryl radical on the carbon atom of the linear alkyl chain, and their respective influence on the properties of the corresponding alkylaryl sulfonates of alkaline earth obtained from these different isomers has been examined. It was thus discovered that the aforementioned drawbacks could be overcome, inasmuch as the mole % of the aryl hydrocarbon, other than benzene, having the aryl substituent on positions 1 or 2 of the linear alkyl chain was between 0 and 13%, and preferably between 5 and 11%, and more particularly between 7 and 10%. This discovery was the subject of U. S. Pat. No. 5,939,594, issued Aug. 17, 1999 to Le Coent.

However, satisfactory results had not been obtained when the aryl hydrocarbon was benzene. Skin formation occurred with the use of benzene, even if the benzene was alkylated with a very long chain linear mono olefin so that the mole % of the aryl hydrocarbon having the aryl substituent on positions 1 or 2 of the linear alkyl chain was between 0 and 13%, and preferably between 5 and 11%, and more particularly between 7 and 10%.

French Patent Application No. 96/10,833 discloses that the aforementioned drawbacks could be overcome by using a mixture of alkylaryl sulfonates of superalkalinized alkaline earth metals comprising:

(a) from 50% to 85% of a linear mono-alkyl phenyl sulfonate in which the linear alkyl chain contains between 14 and 40 carbon atoms, and between 0 and 13 mole % of the phenyl sulfonate radical of the alkaline earth metal is fixed on position 1 or 2 of the linear alkyl chain, and (b) from 15% to 50% of a heavy alkylaryl sulfonate selected from:
  (i) dialkylaryl sulfonates wherein both alkyl substituents are linear alkyl chains, of which the sum of the carbon atoms is from 16 to 40, or
  (ii) mono or polyalkylaryl sulfonates wherein the alkyl substituent or substituents are branched chains, wherein the sum of the carbon atoms is from 15 to 48 carbon atoms.

This mixture of alkylaryl sulfonates has a maximum of 10 mole % of the phenyl sulfonate radical of the alkaline earth metal fixed on position 1 or 2 of the linear alkyl chain. This mixture has no skin formation after three days of storage in an open jar at room temperature. It has good calcium incorporation, a low viscosity, good solubility, and good performance.

European Patent Application No. 98401968.7 discloses a mixture of alkyl phenyl sulfonates of alkaline earth metals having low color and no skin formation even after three days of storage in an open jar at room temperature. That mixture comprises:

(a) from 20% to 70% of a linear mono-alkylphenyl sulfonate in which the linear mono-alkyl substituent contains from 14 to 40 carbon atoms and the mole % of the phenyl sulfonate radical fixed on position 1 or 2 of the linear alkyl chain is between 10% and 25%, and, (b) from 30% to 80% of a branched mono-alkylphenyl sulfonate in which the branched mono alkyl substituent contains from 14 to 18 carbon atoms.

SUMMARY OF THE INVENTION

The present invention provides an alkylaryl composition wherein the aryl radical is other than phenol and wherein the alkyl radical is derived from an isomerized $C_{14}$ to $C_{40}$ normal alpha olefin and wherein either (1) the weight percent of the aryl radical fixed at position 1 or 2 of a linear alkyl chain is less than about 23, or (2) at least 28 weight percent of the alkyl radicals are branched chain alkyl radicals, or (3) both.

Further provided in accordance with this invention is an alkaline earth alkylaryl sulfonate having a Base Number of at least 250, where the aryl radical is other than phenol, wherein the alkyl radical is derived from An isomerized $C_{14}$ to $C_{40}$ normal alpha olefin and wherein either (1) the weight percent of the aryl sulfonate radical fixed at position 1 or 2 of a linear alkyl chain is less than about 23, or (2) at least 28 weight percent of the alkyl radicals are branched chain alkyl radicals, or (3) both.

Also provided in accordance with this invention is an alkaline earth alkylaryl sulfonate having a Base Number of about 2 to about 60, where the aryl radical is other than phenol, wherein the alkyl radical is derived from an isomerized $C_{14}$ to $C_{40}$ normal alpha olefin and wherein either (1) the weight percent of the aryl sulfonate radical fixed at position 1 or 2 of a linear alkyl chain is less than about 23, or (2) at least 28 weight percent of the alkyl radicals are branched chain alkyl radicals, or (3) both.

The present invention also provides a lubricating oil composition comprising a lubricating oil and an alkaline earth alkylaryl sulfonate having a Base Number of at least 250, where the aryl radical is other than phenol, wherein the alkyl radical is derived from an isomerized $C_{14}$ to $C_{40}$ normal alpha olefin and wherein either (1) the weight percent of the aryl sulfonate radical fixed at position 1 or 2 of a linear alkyl chain is less than about 23, or (2) at least 28 weight percent of the alkyl radicals are branched chain alkyl radicals, or (3) both.

Further provided in accordance with this invention is a lubricating oil composition comprising a lubricating oil and an alkaline earth alkylaryl sulfonate having a Base Number of about 2 to about 60, where the aryl radical is other than phenol, wherein the alkyl radical is derived from an isomerized $C_{14}$ to $C_{40}$ normal alpha olefin and wherein either (1) the weight percent of the aryl sulfonate radical fixed at position 1 or 2 of a linear alkyl chain is less than about 23, or (2) at least 28 weight percent of the alkyl radicals are branched chain alkyl radicals, or (3) both.

The present invention also provides a concentrate comprising from about 0.5 wt. % to about 90 wt. % of an alkaline earth alkylaryl sulfonate having a Base Number of at least 250, where the aryl radical is other than phenol, wherein the alkyl radical is derived from an isomerized $C_{14}$ to $C_{40}$ normal alpha olefin and wherein either (1) the weight percent of the aryl sulfonate radical fixed at position 1 or 2 of a linear alkyl chain is less than about 23, or (2) at least 28 weight percent of the alkyl radicals are branched chain alkyl radicals, or (3) both, the balance of the concentrate being an organic liquid diluent compatible with the alkaline earth alkylaryl sulfonate.

Also provided by the present invention is a concentrate comprising from about 0.5 wt. % to about 90 wt. % of an alkaline earth alkylaryl sulfonate having a Base Number of about 2 to about 60, where the aryl radical is other than phenol, wherein the alkyl radical is derived from an isomerized $C_{14}$ to $C_{40}$ normal alpha olefin and wherein either (1) the weight percent of the aryl sulfonate radical fixed at position 1 or 2 of a linear alkyl chain is less than about 23, or (2) at least 28 weight percent of the alkyl radicals are branched chain radicals, or (3) both, the balance of the concentrate being an organic liquid diluent compatible with the alkaline earth alkylaryl sulfonate.

The present invention provides from the same alkylate both a high overbased ("HOB"; BN higher than 250) alkaline earth alkylaryl sulfonate having improved compatibility and solubility, and a low overbased ("LOB"; BN from 2 to 60) alkaline earth alkylaryl sulfonate having good solubility while having low color and no skin formation.

While we have found that a too high concentration of 1-aryl or 2-aryl linear alkylaryl sulfonate causes skin formation in LOB sulfonates, we have found that the higher BN (at least 250 BN) sulfonates are less sensitive to 2-aryl content in the alkylate because the 2-aryl content is diluted by the salts. Therefore, if the BN is high enough (at least 250), and the aryl radical is not phenol, then the weight % of the aryl-sulfonate radical fixed on position 1 or 2 of the linear alkyl chain can be between 2% and 23% (preferably between 13% and 23%) without any skin forming. This high weight percentage of 2-aryl gives a sulfonate having good water absorption properties.

The alkyl chain of the alkaline earth alkylaryl sulfonates of the present invention contains between 14 and 40 carbon atoms, preferably from 20 to 24 carbon atoms.

Some of the alkyl chains of the alkylaryl or alkylaryl sulfonate compositions may be branched. Preferably, at least 28 weight percent, more preferably at least 30 weight percent, of the alkyl radicals are branched chain radicals.

Preferably, the alkaline earth alkylaryl sulfonates of this invention have a mono-alkylate content of at least 87% and an Iodine number of less than 1.0.

Preferably, the alkaline earth alkylaryl sulfonates of this invention are derived from an isomerized $C_{14}$–$C_{40}$ normal alpha olefin, more preferably from isomerized $C_{20}$–$C_{24}$ normal alpha olefin.

The alkaline earth alkylaryl sulfonates of the present invention are preferably derived from an alkylate formed by the reaction of benzene and isomerized normal alpha olefins in the presence of hydrogen fluoride, preferably in a one-stage reactor. Preferably the sulfonate is formed in the presence of methanol and xylene, but preferably in the absence of chlorine (if BN higher than 250).

For BN between 2 and 60 the process used is described in U.S. Pat. No. 4,764,295, issued Aug. 16, 1988 to Le Coent entitled Non-Foaming Detergent-Dispersant Additives for Lubricating Oils and Process for Making Such Additives, which is incorporated by reference herein in its entirety.

A way has been found to have a single alkylation for sulfonates by starting from the same normal alpha olefin having 14 to 40 carbon atoms, preferably from 20 to 24 carbon atoms. Whatever the BN is (from 3 to 500), the following route is used:

(a) Isomerization of NAO $C_{14}$–$C_{40}$, preferably $C_{20}$–$C_{24}$.

At least two types of acidic catalysts can be used for isomerization. The acidic catalyst can be solid or liquid. Preferably, the first type of acidic catalyst is a solid catalyst having at least one metal oxide and having an average pore size of less than 5.5 angstroms. More preferably, it is a molecular sieve with a one-dimensional pore system, such as SM-3, MAPO-11, SAPO-11, SSZ-32, ZSM-23, MAPO-39, SAPO-39, ZSM-22 and SSZ-20. Other possible solid acidic catalysts useful for isomerization include ZSM-35, SUZ4, NU-23, NU-87 and natural or synthetic ferrierites. These molecular sieves are well-known in the art and are discussed in Rosemarie Szostak's *Handbook of Molecular Sieves* (New York, Van Nostrand Reinhold, 1992) and in U.S. Pat. No. 5,282,858, which is hereby incorporated by reference for all purposes. Another type of isomerization catalyst that can be used is iron pentacarbonyl ($Fe(CO)_5$).

The isomerization process may be carried out in batch or continuous mode. The process temperatures can range from 50° C. to 250° C. In the batch mode, a typical method is to use a stirred autoclave or glass flask, which may be heated to the desired reaction temperature. A continuous process is most efficiently carried out in a fixed bed process. Space rates in a fixed bed process can range from 0.1 to 10 or more WHSV. In a fixed bed process, the catalyst is charged to the reactor and activated or dried at a temperature of at least 150° C. under vacuum or flowing inert, dry gas. After activation, the catalyst is cooled to the desired reaction temperature and a flow of the olefin is introduced. The reactor effluent containing the partially branched, isomerized olefin is collected. The resulting partially-branched isomerized olefin contains a different olefin distribution (alpha-olefin, beta-olefin, internal-olefin, trisubstituted olefin and vinylidene-olefin) and branching content than the un-isomerized olefin and conditions are chosen in order to obtain the appropriate structure regarding the level of double bonds between carbon 1 and carbon 2 of the alkyl chain of the olefin (alpha-olefin content).

The appropriate olefin derived from the NAO has less than 15 weight percent alpha content, preferably between 0 and 8 weight percent, with at least 25 weight percent, preferably about 29 to about 60 weight percent of the olefins being branched.

(b) Alkylation

Two routes can be used:

1. Alkylation with HF as a Catalyst

One reactor and a high charge molar ratio benzene/olefin, typically about 10, are used in order to increase the alkylation rate versus isomerization and dimerization rate. The resulting alkylate has a low iodine number and a high level of monoalkylbenzene. As a consequence, a high level of sulfonation can be achieved, leading to an LOB sulfonate (BN between 2 and 60) with no skin formation if stored in an open jar, low viscosity, low color, good solubility, fast rate of filtration and good stability at high temperature. It should be noted in particular that another alkylate (branched or linear dialkyl) is not required to avoid skin formation on the corresponding LOB sulfonates of this invention. Moreover, such an alkylate leads to high overbased sulfonates (at least 250 BN) having good solubility and other properties.

2. Alkylation Using a Solid Acidic Alkylation Catalyst

The alkylation catalyst is a solid catalyst that has at least one metal oxide, which is selected from the group consisting of natural zeolites, synthetic zeolite, synthetic molecular sieves and clays. Preferably, the solid acidic catalyst comprises the acid forms of an acidic clay, or an acidic molecular sieve or a zeolite having an average pore size of at least 6.0 angstroms. Such zeolites include zeolite Y, beta, SSZ-25, SSZ-26 and SSZ-33. Other possible catalysts include L zeolite, mordenite, boggsite, cloverite. VPI-5, MCM-41, MCM-36, SAPO-8, SAPO-5, MAPO-36, SAPO-40, SAPO-41, MAPSO-46, CoAPO-50, hexagonal faujasite, ECM-2, gmelinite, mazzite (omega zeolite), offretite, ZSM-18 and ZSM-12. These catalysts are discussed in Rosemarie Szostak's Handbook of Molecular Sieves (New York, Van Nostrand Reinhold, 1992). More preferably, the solid acidic catalyst comprises zeolite Y. A preferred zeolite Y has a silica to alumina ratio of at least 40:1.

Useful acidic clays may be derived from naturally occurring or synthetic materials. One skilled in the art would realize that there are a number of such clays that are known to be alkylation catalysts. Examples of such acidic clays include montmorillonite, laponite and saponite. Pillared clays may also be used as catalysts.

The alkylation reaction is typically carried out with an aromatic and an olefin in molar ratios from 1:15 to 25:1. The process temperatures can range from 100° C. to 250° C. As the olefins have a high boiling point, the process is preferably carried out in the liquid phase. The alkylation process may be carried out in batch or continuous mode. In the batch mode, a typical method is to use a stirred autoclave or glass flask which may be heated to the desired reaction temperature. A continuous process is most efficiently carried out in a fixed bed process. Space rates in a fixed bed process can range from 0.1 to 10 or more WHSV. In a fixed bed process, the catalyst is charged to the reactor and activated or dried at a temperature of at least 150° C. under vacuum or flowing inert dry, gas. After activation, the catalyst is cooled to the desired reaction temperature and a flow of the aromatic compound is introduced. Pressure is increased by means of a back pressure valve so that the pressure is above the bubble point pressure of the feed composition at the desired reaction temperature. After pressurizing the system to the desired pressure, the temperature is increased to the desired reaction temperature. Optionally, the aromatic may be added to the catalyst at reaction temperature. A flow of the olefin is then mixed with the aromatic and allowed to flow over the catalyst. The reactor effluent containing alkylate product and excess aromatic is collected. Excess aromatic is then removed by distillation, stripping evaporation under vacuum or other means know to those skilled in the art.

DETAILED DESCRIPTION OF THE INVENTION

In its broadest aspect, the present invention involves an alkylaryl composition, an alkaline earth alkylaryl sulfonate, methods for its preparation, and its application as a detergent/dispersant additive for lubricating oils.

Prior to discussing the invention in further detail, the following terms will be defined:

DEFINITIONS

As used herein the following terms have the following meanings unless expressly stated to the contrary:

The term "alkylaryl composition" refers to a hydrocarbon or mixture of hydrocarbons each comprising an aryl group, such as benzyl, tolyl, or ortho-xylyl having attached directly to it one or more $C_{14}$ to $C_{40}$ alkyl groups.

The term "alkaline earth metal" refers to calcium, barium, magnesium and strontium.

The term "alkaline earth alkylaryl sulfonate" refers to an alkaline earth metal salt of an alkylaryl sulfonic acid. In other words, it is an alkaline earth metal salt of an aryl that is substituted with (1) an alkyl group and (2) a sulfonic acid group that is capable of forming a metal salt.

The term "the weight % of the aryl sulfonate radical on position 1 or 2 of a linear alkyl chain" refers to the weight percentage of all the aryl sulfonate radicals fixed on a linear alkyl chain that are fixed at the first or second position of the linear alkyl chain. The first position of the linear alkyl chain is the position at the end of the chain. The second position of the linear alkyl chain is the position immediately next to the first position.

The term "1-aryl" refers to an aryl sulfonate radical fixed on a linear alkyl chain at the first position of the linear alkyl chain.

The term "2-aryl" refers to an aryl sulfonate radical fixed on a linear alkyl chain at the second position of the linear alkyl chain.

The term "monoalkylate content" is the weight percentage of the alkylate that is not dialkylate (100×monoalkylate/(monoalkylate+dialkylate)).

The term "Iodine Number" is the absorption value (Hübl Number or Wijs number), which is the quantity of iodine, in grams, absorbed by 100 grams of fat or oil under specified conditions. It indicates the amount of double bonds present.

The term "Base Number" or "BN" refers to the amount of base equivalent to milligrams of KOH in one gram of sample. Thus, higher BN numbers reflect more alkaline products, and therefore a greater alkalinity reserve. The BN of sample can be determined by ASTM Test No. D2896 or any other equivalent procedure.

The term "overbased alkaline earth alkylaryl sulfonate" refers to a composition comprising a diluent (e.g., lubricating oil) and an alkylaryl sulfonate wherein additional alkalinity is provided by a stoichiometric excess of an alkaline earth metal base, based on the amount required to react with the acidic moiety of the sulfonate. Enough diluent should be incorporated in the overbased sulfonate to ensure easy handling at safe operating temperatures.

The term "low overbased alkylaryl sulfonate" refers to an overbased alkaline earth alkylaryl sulfonate having a BN of about 2 to about 60.

The term "high overbased alkaline earth sulfonate" refers to an overbased alkaline earth alkylaryl sulfonate having a BN of 250 or more. Generally a carbon dioxide treatment is required to obtain high BN overbased detergent compositions. It is believed that this forms a colloidal dispersion of metal base.

Unless otherwise specified, all percentages are in weight percent, all ratios are molar ratios, and all molecular weights are number average molecular weights.

ALKYLARYL COMPOSITION

The alkylaryl composition (or "alkylate") can be formed by the reaction of an aryl compound, such as benzene or toluene, and isomerized, normal alpha olefin in the presence of hydrogen fluoride, preferably in a one-stage reactor.

ALKYLARYL SULFONATES

The alkylaryl sulfonates of the present invention are high or low overbased alkaline earth alkylaryl sulfonates having linear alkyl groups. These alkylaryl sulfonates have improved compatibility and solubility, while having low color and no skin formation.

The alkylaryl sulfonates are high overbased (BN of at least 250), or low overbased sulfonates (BN from 2 to 60—preferably from 5 to 30).

It is also essential that the aryl radical is not phenol, since high overbased alkylphenoxy sulfonates having 2-aryl content tend to be too viscous for easy handling. Preferably, it is an alkyl benzene sulfonate or an alkyl toluene sulfonate.

The linear alkyl chain contains between 14 and 40 carbon atoms, preferably from 20 to 24 carbon atoms. Preferably, the alkaline earth alkylaryl sulfonate is derived from an isomerized $C_{14}$–$C_{40}$ normal alpha olefin, more preferably from an isomerized $C_{20}$–$C_{24}$ normal alpha olefin.

Preferably, the alkaline earth alkylaryl sulfonate has a monoalkylate content of at least 87% and an iodine number of less than 1.0.

Aforementioned U.S. Pat. No. 4,764,295 describes alkylaryl sulfonates of alkaline earth metals resulting from alkylation by a linear olefin.

Preferably, the highly overbased alkaline earth alkylaryl sulfonate is formed in the presence of methanol and xylene, and in the absence of chlorine. The process for preparing low overbased alkaline earth alkylaryl sulfonates is described in aforementioned U.S. Pat. No. 4,764,295.

Preferably, the alkaline earth alkylaryl sulfonate is used in a lubricant in conjunction with another detergent, preferably a sulfurized alkaline earth alkylaryl phenate.

EXAMPLES

The invention will be further illustrated by the following examples, which set forth particularly advantageous method embodiments. While the examples are provided to illustrate the present invention, they are not intended to limit it.

METHODS OF MEASUREMENTS

The examples contain test results obtained by the following methods of measurement:

Viscosity at 100° C. in mm$^2$/S a) In the Case of High Overbased Alkylaryl Sulfonates:

The viscosity was measured at the temperature of 100° C. after dilution of the product sample to be measured in 600 N oil, until a solution was obtained having a total calcium content of 15.5%.

b) In the Case of Low Overbased Alkylaryl Sulfonates:

The viscosity was measured at the temperature of 100° C. after dilution of the product to be measured in 100 N oil, until a solution was obtained having a total calcium content of 2.35%.

The viscosity was measured following method ASTM D 445 in both cases.

Compatibility

Two methods were used to evaluate the appearance and the storage stability of the additives and the corresponding oils containing them. These methods are applicable to additives for lubricants.

a) In the Case of High Overbased Alkylaryl Sulfonates:

Method No. 1: Accelerated Stability Storage Test (ASST)

Procedure:

Form a blend of 100 grams of the following products in a 250 ml beaker:
  A 250 BN phenate in a quantity such that the BN coming from the phenate in the 100 gram blend is 35.
  A 400 BN sulfonate (or a 320 BN sulfonate) in a quantity such that the BN coming from the sulfonate in the 100 gram blend is 35.
  35 grams of diluent oil named 150 bright stock (from Idemitsu Kosan Company).

Blend for 30 minutes at 65° C., then put the oil obtained into a centrifuge tube. Keep it in an oven for 24 hours at 100° C. then centrifuge for one hour at 4540 rpm.

Read the sediment content. If the sediment content is less than 0.05% of the oil the results are a "pass", otherwise it is a "fail".

Specifications:
(1) for clear and bright product
(2) for a very slightly product
(3) for a turbid product
  Specifications (1) and (2) are considered as product "in specification".
  Specification (3) is considered as product "off specification".

b) In the Case of a Low Overbased Alkylaryl Sulfonates:

An additive is prepared based on monosuccinimide and zinc dithiophosphate and containing about 75% by weight of the mixture of sulfonates to be tested. The additive is placed in a 350 neutral oil base stock in order to obtain a solution containing 10% by weight of the additive. The appearance of the product is evaluated after 30 days at ambient temperature. The appearance of the product is evaluated before and after storage, and the results are qualified as "good" or "poor" according to whether or not a single phase is maintained without any deposit of sediment.

Color Test

A color test (ASTM D1500) was performed on the sulfonate prior to blending.

PROCEDURE FOR DETERMINING THE % LINEAR 1- AND 2-ARYL ATTACHMENT IN ALKYLATES BY GAS CHROMATOGRAPHY MASS SPECTROMETRY (GCMS)

A Hewlett Packard Model 5890 gas chromatograph (GC) in conjunction with a Hewlett Packard Model 5970 Mass Selective Detector (MSD) was used to perform the GCMS experiments. The GC was fitted with a capillary column (60 m×0.2 mm ID×0.5 micron DB-1) operating with nitrogen carrier gas, 300° C. injector temperature, a 100:1 split injection and the following oven temperature program: 60 to 320° C. at 5° C./min hold at 320° C. for 10 minutes. The MSD operated at 325° C. and 3.6×10$^{-5}$ torr vacuum.

To determine the % linear 2-phenyl attachment molecular species present in an alkyl benzene alkylate, the m/e=90 and 105 peak for the primary fragmentation ion for 1- and 2-phenyl alkyl benzene molecules was monitored and those peaks corresponding to the 1- and 2-phenyl alkyl benzene species was integrated from the total ion current (TIC) chromatogram using the following equation:

$$\% \text{ 1- and 2-Phenyl Attachment} = \frac{TIC \text{ for 1- and 2-Phenyl Peaks}}{TIC \text{ for All Alkylate Peaks}}$$

Likewise, to determine the quantity of linear 2-tolyl attachment molecular species present in an alkylate, the m/e=105 and 119 for the primary fragmentation ion for the 2-tolyl alkyl toluene alkylate molecules.

PROCEDURE FOR DETERMINING THE WEIGHT % BRANCHING OF THE ALKYL CHAIN OF AN ALKYLATE BY INFRARED SPECTROMETRY (IR)

The procedure is based on using the absorbance at 1378 $cm^{-1}$ due to the C—$CH_3$ symmetric deformation as a measure of the branching along the alkyl chain of an alkylate sample. The measurement is not an absolute measurement but is based on a calibration curve of the absorbance of a known concentration of sample in chloroform in a liquid IR cell of a given path length at 1378 $cm^{-1}$ versus weight % branching content. Reference standards were prepared from samples of isomerized $C_{20-24}$ NAO samples that had been hydrogenated and analyzed by Gas Liquid Phase Chromatography (GLPC) to determine the weight % branching content. The procedure for determining the absorbance of the sample was to dissolve 50 weight % of the sample into chloroform (Spectral Grade) and placing the sample in a liquid IR cell of given pathlength. A background spectrum was obtained using a blank ($N_2$). The absorption spectrum between 1200 $cm^{-1}$ and 1600 $cm^{-1}$ was obtained and the region between 1200 $cm^{-1}$ and 1400 $cm^{-1}$ cm was expanded and a base line drawn between the valleys that occur at approximately 1395 $cm^{-1}$ and 1325 $cm^{-1}$. Then the absorbance from the baseline to the top of the peak at 1378 $cm^{-1}$ was measured. The weight percent branching was then determined from the calibration curve generated with the reference standards.

PROCEDURE FOR SYNTHESIS OF ALKYLATE

Synthesis of the Alkylate

The alkylate was synthesized in an alkylation pilot plant with hydrofluoric acid, which consisted of two reactors in series of 1.150 liters each, and a 25 liter settler wherein the organic phase was separated from the phase containing the hydrofluoric acid, all of the equipment being maintained under a pressure of about $5 \times 10^5$ Pa.

The organic phase was then withdrawn via a valve, and expanded to atmospheric pressure, and the benzene was removed by topping, that means by heating to 160° C. at atmospheric pressure.

After withdrawal, the mineral phase was neutralized by caustic potash.

The reaction was carried out in either one or two reactors:
If only one reactor was used, the benzene/olefin mole ratio was 10:1, which was very high, and the second reactor was by-passed. This is the preferred method.
If two reactors were used, the benzene/olefin mole ratio was relatively low in the first reactor, about 1:1 to 1.5:1, and it was higher in the second reactor, about 2:1 to 10:1. Furthermore, the ratio of hydrofluoric acid to the olefin by volume was about 1:1 in the first reactor and about 2:1 in the second reactor.

Distillation of the Alkylate

As benzene was alkylated by a $C_{20}$ to $C_{24}$ linear olefin, there was no formation of a light fraction. Hence it was sufficient to effect a topping of the unreacted benzene and residual hydrofluoric acid to obtain the corresponding alkylate.

Sulfonation of the Alkylate

The molar proportion of the phenyl radical substituted on the carbon atoms in position 1 or 2 of the alkyl radical was determined on the alkylate, then the alkylate was subjected to the sulfonation reaction.

Sulfonation was conducted on the alkylate using sulfur trioxide ($SO_3$), produced by the passage of a mixture of oxygen and sulfur dioxide ($SO_2$) through a catalytic furnace containing vanadium oxide ($V_2O_5$). The sulfur trioxide gas was introduced at the top of a sulfonation reactor (2 meter long and 1 cm in diameter) in a concurrent alkylate stream.

The resulting sulfonic acid was recovered at the bottom of the reactor. The sulfonation conditions are as follow:

The $SO_3$ flow rate was set at 76 grams/hour.

The alkylates flow rate was between 300 and 450 grams/hour, depending on the desired SO3:alkylate mole ratio, which varied from 0.8:1 to 1.2:1.

The sulfonation temperature was between 50° and 60° C.

Nitrogen was used as vector gas to dilute the $SO_3$ to 4% by volume.

After the sulfonation reaction, the residual sulfuric acid was removed by thermal treatment after dilution by 10% 100 N oil, nitrogen bubbling at the rate of 10 liter/hour per Kg of product, and stirring at 85° C., until a lower residual $H_2SO_4$ content was obtained (maximum 0.5% by weight).

Superalkalinization for High Overbased Sulfonates

In this step, hydrated lime $Ca(OH)_2$ was added to the reaction product at a very high molar ratio of hydrated lime versus sulfonic acid, and the product was reacted in order to obtain a final product having a BN higher than 250 (preferably between 300 and 430) according to standard ASTM D 2896. To obtain this, a quantity of $Ca(OH)_2$ was added in large excess to the stoichiometric neutralization of the quantity of sulfonic acid reacted (0.5 mole of $Ca(OH)_2$ per mole of this sulfonic acid). The lime reagent was methanol and the solvent was xylene. The carbonation was carried out by $CO_2$ at a temperature between 20° and 55° C. Before elimination of the solvent, the sediment was eliminated by centrifugation.

The performance obtained by the alkyl aryl sulfonate mixture of the invention are summarized in the table given at the end of the present specification.

Low Overbased Sulfonates BN 2-60

LOB sulfonates can be made by the method disclosed in U. S. Pat. No. 4,764,295, issued Aug. 16, 1988 to Le Coent (which is incorporated by reference herein). The method involves the following steps:

(a) reacting, in a diluent oil, an alkylaryl sulfonic acid with an alkaline earth base, the amounts of reactants used being such that the molar ratio of the alkaline earth base to the alkylaryl sulfonic acid in the reaction medium is between about 0.51 and about 1.8;

(b) contacting the materials specified in step (a) (or their reaction product) with an alcohol having a boiling point above about 80° C., in the presence of water and chloride ions, with the molar ratios of the constituents being:

(i) for the chloride ion to the alkylaryl sulfonic acid, between about 0.005 and about 0.02;

(ii) for the alcohol to the alkylaryl sulfonic acid, greater than or equal to about 0.1; and (iii) for the water to the alkylaryl sulfonic acid, between about 0.2 and about 5;

(c) removing water and alcohol from the product obtained in step (b); and (d) removing solid substances from the product obtained in step (c) (e.g., by filtration or centrifuging, preferably by filtration).

The following examples are provided to illustrate the present invention, and are not intended to limit it.

Example 1
PRE-ISOMERIZATION OF A $C_{20-24}$ NORMAL ALPHA OLEFIN—FLOW REACTOR.

$C_{20-24}$ Normal Alpha Olefin (89.1% alpha-olefin by carbon NMR and 11% branching by IR) is pre-heated by pumping through a heated (350° C.) tube containing 24 mesh Alundum and then into (up-flow) an unheated fixed bed reactor (84 cm long×2.26 cm ID) containing 216 gm of 1/8" circular SAPO-11 extrudate co-packed with 255 gm of 100 mesh Alundum at a flow rate of approximately 5 gm/min. The skin temperature of the fixed bed reactor is nominally 215° C. The isomerized olefin product is collected and regular samples are collected and analyzed as follows:

| Sample | 1 | 2 | 3 | 4 |
|---|---|---|---|---|
| Amount Collected (kg) | 5.52 | 5.63 | 5.46 | 5.50 |
| Wt. % Alpha-Olefin | 4.0 | 3.0 | 6.0 | 3.0 |
| Wt. % Branching | 33 | 40 | 38 | 30 |

Example 2

In a 1.15 liter reactor, stirred and heated by a double jacket to 64° C., are added continuously HF (as catalyst) at 21.45 ml/minute, isomerized $C_{20}$–$C_{24}$ normal alpha olefin characterized by a level of 2% alpha content and 48% branched-chain olefins at 26.81 ml/minute, and benzene at 66.75 ml/minute. This corresponds to a benzene/isomerized olefin mole ratio of 10:1, and a HF/isomerized olefin volume ratio of 0.8:1. An unheated settler is used to recover the organic phase and to recycle a portion of the HF catalyst to the reactor. The pressure in the reactor and settler is maintained a $5×10^5$ Pa.

The excess benzene is distilled by passage through a preheater at 120° C. and introduction into the bottom of a column at 260° C. As benzene is alkylated by the isomerized olefin, there is no formation of light. Hence, it is sufficient to effect topping of the unreacted benzene and residual HF to obtain the corresponding alkylate.

Sulfonation is conducted on the alkylate using sulfur trioxide produced by the passage of a mixture of oxygen and sulfur dioxide through a catalytic furnace containing vanadium oxide ($V_2O_5$). The sulfur trioxide gas is introduced at the top of a sulfonation reactor (2 meters long and 1 cm in diameter) in a co-current alkylate stream. The sulfonic acid is recovered at the bottom of the reactor. The sulfonation conditions are as follows:

Sulfur trioxide flow rate is set at 71 grams/hour

Alkylate flow rate is 320 grams/hour

Sulfur trioxide/alkylate mole ratio is 1.05:1.

Sulfonation temperature is 55° C.

Nitrogen is used as vector gas to dilute sulfur trioxide to 4% by volume.

After the sulfonation reaction, the residual sulfuric acid is removed by thermal treatment by 10% 100 N diluent, nitrogen bubbling at the rate of 10 liters/hour per kg of product and stirring at 85° C., until a lower residual sulfuric acid is obtained (maximum 0.5% by weight).

Comparative Example A

The procedure of Example 1 is repeated, except that a $C_{20}$–$C_{24}$ normal alpha olefin is used instead of the isomerized olefin of Example 1. For the LOB sulfonates, incorporation of lime is poor, the crude sediment is high, compatibility is poor, viscosity is high and a skin forms on the product.

Comparative Example B
TWO STAGE, TWO REACTORS

Table I below shows the results of the alkylations in Example 2 and Comparative Examples A and B, and the properties of LOB sulfonates made from the alkylates.

TABLE I

|  |  | Example 2 | Comp. Ex. A | Comp. Ex. B |
|---|---|---|---|---|
| Alkylation | Aromatic | Benzene | Benzene | Benzene |
|  | Olefin | Isomerized $C_{20-24}$ NAO | $C_{20-24}$ NAO | $C_{20-24}$ NAO |
|  | Catalyst | HF | HF | HF |
| Reactor 1 | Catalyst/Olefin (vol.) | 0.8 | 0.8 | 0.3 |
|  | Aromatic/Olefin (mole) | 10 | 10 | 1.2 |
| Reactor 2 | Catalyst/Olefin (vol.) |  |  | 0.5 |
|  | Aromatic/Olefin (mole) |  |  | 5.8 |
| Analysis of alkylate | Wt. % Unreacted olefin | 0.2 | 0.2 | 0.39 |
|  | Wt. % Linear 1- and 2-phenyl | 2.1 | 25.8 | 9.7 |
|  | Wt. % Branching of the alkyl chain in the alkylate | 42.9 | 23.2 | 26.4 |

TABLE I-continued

|  |  | Example 2 | Comp. Ex. A | Comp. Ex. B |
|---|---|---|---|---|
| Analysis of sulfonic acid after thermal treatment | Wt. % $HSO_3$ | 15.7 | 15.8 | 15.1 |
|  | Wt. % $H_2SO_4$ | 0.1 | 0.1 | 0.1 |
| Analysis of LOB sulfonate | Crude sediment (wt. %) before filtration | 0.6 | 2 | 1 |
|  | Wt. % CaT | 2.64 | 2.3 | 2.64 |
|  | Wt. % CaS | 1.75 | 1.65 | 1.75 |
|  | BN (ASTM D 2896) | 18.2 | 14 | 18.2 |
|  | Compatibility | Good | Poor | Good |
|  | Visc. @ 100° C. $mm^2$/s @ 2.35% CaT | 23 | Too viscous to be measured | 25 |
|  | wt. % Sediment after filtration | 0.02 | 0.3 | 0.2 |
|  | Filtration rate (Kg/h per $m^2$) | 700 | 50 | 80 |
|  | Skin formation in open air | No | Yes, after 2 hrs. | Yes, after 1 day |

Table II below shows the properties of HOB sulfonates made from the alkylates of Example 1 and Comparative Examples A and B.

TABLE II

|  |  | Example 1 | Comp. Ex. A | Comp. Ex. B |
|---|---|---|---|---|
| Analysis of sulfonic acid after thermal treatment | Wt. % $HSO_3$ | 15.7 | 15.8 | 15.1 |
|  | Wt. % $H_2SO_4$ | 0.1 | 0.1 | 0.1 |
| Analysis of HOB sulfonate | Wt. % CaT | 15.8 | 15.8 | 15.8 |
|  | BN (ASTM D 2896) | 418 | 418 | 418 |
|  | Compatibility Method 1 | Pass | Pass | Fail |

What is claimed is:

1. An alkylaryl composition wherein the aryl radical comprises benzyl and wherein the alkyl radical is derived from an isomerized $C_{14}$ to $C_{40}$ normal alpha olefin and wherein the weight percent of the aryl radical fixed at position 1 or 2 of a linear alkyl chain is less than about 23 and wherein at least 28 weight percent of the alkyl radicals are branched chain alkyl radicals.

2. The alkylaryl composition of claim 1 wherein the weight percent of the aryl radical fixed at position 1 or 2 of a linear alkyl chain is about 2 weight percent to about 23 weight percent and the branched chain alkyl radicals are methyl-branched.

3. The alkylaryl composition of claim 1 wherein the weight percent of the aryl radical fixed at position 1 or 2 of a linear alkyl chain is between about 2 weight percent and about 23 weight percent, and about 28 weight percent to about 50 weight percent of the alkyl radicals are branched chain alkyl radicals.

4. The alkylaryl composition of claim 1 wherein the isomerized normal alpha olefin has an alpha content of less than 15 weight percent and at least 25 weight percent of the olefins are branched chain olefins.

5. The alkylaryl composition of claim 1 wherein the isomerized normal alpha olefin has an alpha content of about 0 to about 8 weight percent and about 29 weight percent to about 60 weight percent of the olefins are branched chain olefins.

6. The alkylaryl composition of claim 1 wherein the alkyl radical is derived from a linear $C_{20}$ to $C_{24}$ isomerized normal alpha olefin.

7. The alkylaryl composition of claim 1 or 6 having a monoalkylate content of at least 87%.

8. An alkaline earth alkylaryl sulfonate having a Base Number of at least 250, wherein the aryl radical comprises benzyl, wherein the alkyl radical is derived from an isomerized $C_{14}$ to $C_{40}$ normal alpha olefin and wherein the weight percent of the aryl sulfonate radical fixed at position 1 or 2 of a linear alkyl chain is less than about 23 and wherein at least 28 weight percent of the alkyl radicals are branched chain alkyl radicals.

9. An alkaline earth alkylaryl sulfonate having a Base Number of about 2 to about 60, where the aryl radical comprises benzyl, wherein the alkyl radical is derived from an isomerized $C_{14}$ to $C_{40}$ normal alpha olefin and wherein the weight percent of the aryl sulfonate radical fixed at position 1 or 2 of a linear alkyl chain is less than about 23 and wherein at least 28 weight percent of the alkyl radicals are branched chain alkyl radicals.

10. The alkaline earth alkylaryl sulfonate of claim 8 or 9 wherein the weight percent of the aryl radical fixed at position 1 or 2 of a linear alkyl chain is between about 2 weight percent and about 23 weight percent, and the branched chain alkyl radicals are methyl-branched.

11. The alkaline earth alkylaryl sulfonate of claim 8 or 9 wherein the weight percent of the aryl sulfonate radical fixed at position 1 or 2 of a linear alkyl chain is between about 2 weight percent and about 23 weight percent, and about 28 weight percent to about 50 weight percent of the alkyl radicals are branched chain alkyl radicals.

12. The alkaline earth alkylaryl sulfonate of claim 8 or 9 wherein the isomerized normal alpha olefin has an alpha content of less than 15 weight percent and at least 25 weight percent of the olefins are branched chain.

13. The alkaline earth alkylaryl sulfonate of claim 8 or 9 wherein the isomerized normal alpha olefin has an alpha content of about 0 to about 8 weight percent, and about 29 weight percent to about 60 weight percent of the olefins are branched chain olefins.

14. The alkaline earth alkylaryl sulfonate of claim 8 or 9 wherein the aryl radical is benzyl, tolyl, or ortho-xylyl.

15. The alkaline earth alkylaryl sulfonate of claim 14 wherein the aryl radical is benzyl.

16. The alkaline earth alkylaryl sulfonate of claim 8 or 9 wherein the alkyl radical is derived from an isomerized $C_{20}$ to $C_{24}$ normal alpha olefin.

17. The alkaline earth alkylaryl sulfonate of claim 8 or 9 wherein said alkaline earth alkylaryl sulfonate has a monoalkylate content of at least 87% and an Iodine Number of less than 1.0.

18. A lubricating oil composition comprising a lubricating oil and an alkaline earth alkylaryl sulfonate having a Base Number of at least 250, wherein the aryl radical comprises benzyl wherein the alkyl radical is derived from an isomerized $C_{14}$ to $C_{40}$ normal alpha olefin and wherein the weight percent of the aryl sulfonate radical fixed at position 1 or 2 of a linear alkyl chain is less than about 23 and wherein at least 28 weight percent of the alkyl radicals are branched chain alkyl radicals.

19. A lubricating oil composition comprising a lubricating oil and an alkaline earth alkylaryl sulfonate having a Base Number of about 2 to about 60, wherein the aryl radical comprises benzyl, wherein the alkyl radical is derived from an isomerized $C_{14}$ to $C_{40}$ normal alpha olefin and wherein the weight percent of the aryl sulfonate radical fixed at position 1 or 2 of a linear alkyl chain is less than about 23 and wherein at least 28 weight percent of the alkyl radicals are branched chain alkyl radicals.

20. The lubricating oil composition of claim 18 or 19 wherein the weight percent of the aryl radical fixed at position 1 or 2 of a linear alkyl chain is between about 2% and about 23%, and the branched chain alkyl radicals are methyl-branched.

21. The lubricating oil composition of claim 20 or 19 wherein the weight percent of the aryl sulfonate radical fixed at position 1 or 2 of a linear alkyl chain is between about 2 weight percent and about 23 weight percent, and about 28 weight percent to about 50 weight percent of the alkyl radicals are branched chain radicals.

22. The lubricating oil composition of claim 20 or 19 wherein the isomerized normal alpha olefin has an alpha content of less than 15 weight percent, and at least 25 weight percent of the olefins are branched chain olefins.

23. The lubricating oil composition of claim 20 or 19 wherein the isomerized normal alpha olefin has an alpha content of about 0 to about 8 weight percent, and about 29 weight percent to about 60 weight percent of the olefins are branched chain olefins.

24. The lubricating oil composition of claim 20 or 19 wherein the alkyl radical is derived from an isomerized $C_{20}$ to $C_{24}$ normal alpha olefin.

25. The lubricating oil composition of claim 20 or 19 wherein said alkaline earth alkylaryl sulfonate has a monoalkylate content of at least 87% and an Iodine Number of less than 1.0.

26. The lubricating oil composition of claim 20 or 19 wherein the alkaline earth alkylaryl sulfonate is the only alkaline earth alkylaryl sulfonate in the composition.

27. A concentrate comprising from about 0.5 wt. % to about 90 wt. % of an alkaline earth alkylaryl sulfonate having a Base Number of at least 250, wherein the aryl radical comprises benzyl, wherein the alkyl radical is derived from an isomerized $C_{14}$ to $C_{40}$ normal alpha olefin and wherein the weight percent of the aryl sulfonate radical fixed at position 1 or 2 of a linear alkyl chain is less than about 23 and wherein at least 28 weight percent of the alkyl radicals are branched chain radicals, the balance of the concentrate being an organic liquid diluent compatible with the alkaline earth alkylaryl sulfonate.

28. A concentrate comprising from about 0.5 wt. % to about 90 wt. % of an alkaline earth alkylaryl sulfonate having a Base Number of about 2 to about 60, wherein the aryl radical comprises benzyl, wherein the alkyl radical is derived from an isomerized $C_{14}$ to $C_{40}$ normal alpha olefin and wherein the weight percent of the aryl sulfonate radical fixed at position 1 or 2 of a linear alkyl chain is less than about 23 and wherein at least 28 weight percent of the alkyl radicals are branched chain radicals, the balance of the concentrate being an organic liquid diluent compatible with the alkaline earth alkylaryl sulfonate.

29. The concentrate of claim 27 or 28 wherein the weight percent of the aryl radical fixed at position 1 or 2 of the alkyl chain is between about 2 weight percent and about 23 weight percent, and the branched chain alkyl radicals are methyl-branched.

30. The concentrate of claim 27 or 28 wherein the weight percent of the aryl sulfonate radical fixed at position 1 or 2 of a linear alkyl chain is between about 2 weight percent and about 23 weight percent, and about 28 weight percent to about 50 weight percent of the alkyl radicals are branched chain alkyl radicals.

31. The concentrate of claim 27 or 28 wherein the isomerized normal alpha olefin has an alpha content of less than 15 weight percent, and at least 25 weight percent of the olefins are branched chain olefins.

32. The concentrate of claim 27 or 28 wherein the isomerized normal alpha olefin has an alpha content of about 0 to about 8 weight percent, and about 29 weight percent to about 60 weight percent of the olefins are branched chain olefins.

33. The concentrate of claim 27 or 28 wherein the alkyl radical is derived from an isomerized $C_{20}$ to $C_{24}$ normal alpha olefin.

34. The concentrate of claim 27 or 28 wherein said alkaline earth alkylaryl sulfonate has a monoalkylate content of at least 87% and an Iodine Number of less than 1.0.

35. The concentrate of claim 27 or 28, wherein the alkaline earth alkylaryl sulfonate is the only alkaline earth alkylaryl sulfonate in the composition.

\* \* \* \* \*